United States Patent [19]

Argoudelis et al.

[11] 4,335,108

[45] Jun. 15, 1982

[54] PAULOMYCIN A AND B AND PREPARATION THEREOF

[75] Inventors: Alexander D. Argoudelis, Portage; Vincent P. Marshall, Kalamazoo; Leroy E. Johnson, Kalamazoo Township, Kalamazoo County, all of Mich.

[73] Assignee: The Upjohn Company, Kalamazoo, Mich.

[21] Appl. No.: 180,682

[22] Filed: Aug. 25, 1980

[51] Int. Cl.$^3$ .................. A61K 35/00; C12P 1/06; C12N 1/20
[52] U.S. Cl. ..................... 424/117; 424/123; 424/124; 435/169; 435/253
[58] Field of Search ............... 435/169, 253; 424/117, 424/123, 124

[56] References Cited

U.S. PATENT DOCUMENTS

| | | | |
|---|---|---|---|
| 3,966,913 | 6/1976 | Ito et al. | 424/119 |
| 3,988,441 | 10/1976 | Hanka et al. | 424/117 |
| 3,988,441 | 10/1976 | Hanka et al. | 424/117 |
| 4,029,769 | 6/1977 | Debono | 424/118 |
| 4,032,632 | 6/1977 | Celmer et al. | 424/121 |
| 4,110,435 | 8/1978 | Nakatsukasa et al. | 424/122 |

*Primary Examiner*—Alvin E. Tanenholtz
*Assistant Examiner*—James Martinell
*Attorney, Agent, or Firm*—Roman Saliwanchik

[57] ABSTRACT

Disclosed and claimed is an improved fermentation process for preparing the known antibiotic U-43,120, herein referred to as paulomycin. Also disclosed and claimed are the novel and useful antibiotics paulomycin A and paulomycin B.

10 Claims, 7 Drawing Figures

Brinkman's Cellulose MN 400;
pH 7.0 phosphate buffer

PAULOMYCIN A AND B AND PREPARATION THEREOF

BACKGROUND OF THE INVENTION

The production of antibiotic U-43,120 by *Streptomyces paulus*, NRRL 8115, and the physicochemical properties of this compound are described in U.S. Pat. No. 3,988,441 (Oct. 26, 1976). Recent work by us shows, unexpectedly, that antibiotic U-43,120, which we have now named paulomycin, is a mixture of two chemically related antibiotics. We have named these two new antibiotic entities paulomycin A and paulomycin B.

BRIEF SUMMARY OF THE INVENTION

An improved fermentation process for preparing paulomycin has been discovered. This process uses a biologically pure culture of a newly-discovered strain of *S. paulus*. This new man-made culture has been designated *S. paulus* strain 273.

We have also discovered, unexpectedly, that paulomycin is a mixture of two chemically related antibiotics. These new and useful antibiotics have been named paulomycin A and paulomycin B.

Paulomycin A and B have the properties of adversely affecting the growth of Gram-positive bacteria, for example *Bacillus subtilis, Staphylococcus aureus, Streptococcus pyogenes* and *Streptococcus faecalis*. Thus, they can be used alone or in combination with other antibacterial agents to prevent the growth of, or reduce the number of, such microorganisms present in various environments. Also, they are useful in wash solutions for sanitation purposes, as in the washing of hands and in the cleaning of equipment, floors, or furnishings of contaminated rooms or laboratories; they are also useful as an industrial preservative, for example, as a bacteriostatic rinse for laundered clothes and for impregnating papers and fabrics; and they are useful for suppressing the growth of sensitive organisms in plate assays and other microbiological media.

DETAILED DESCRIPTION OF THE INVENTION

Chemical and Physical Properties of Paulomycin A

Infrared Absorption Spectrum

Figure 1:
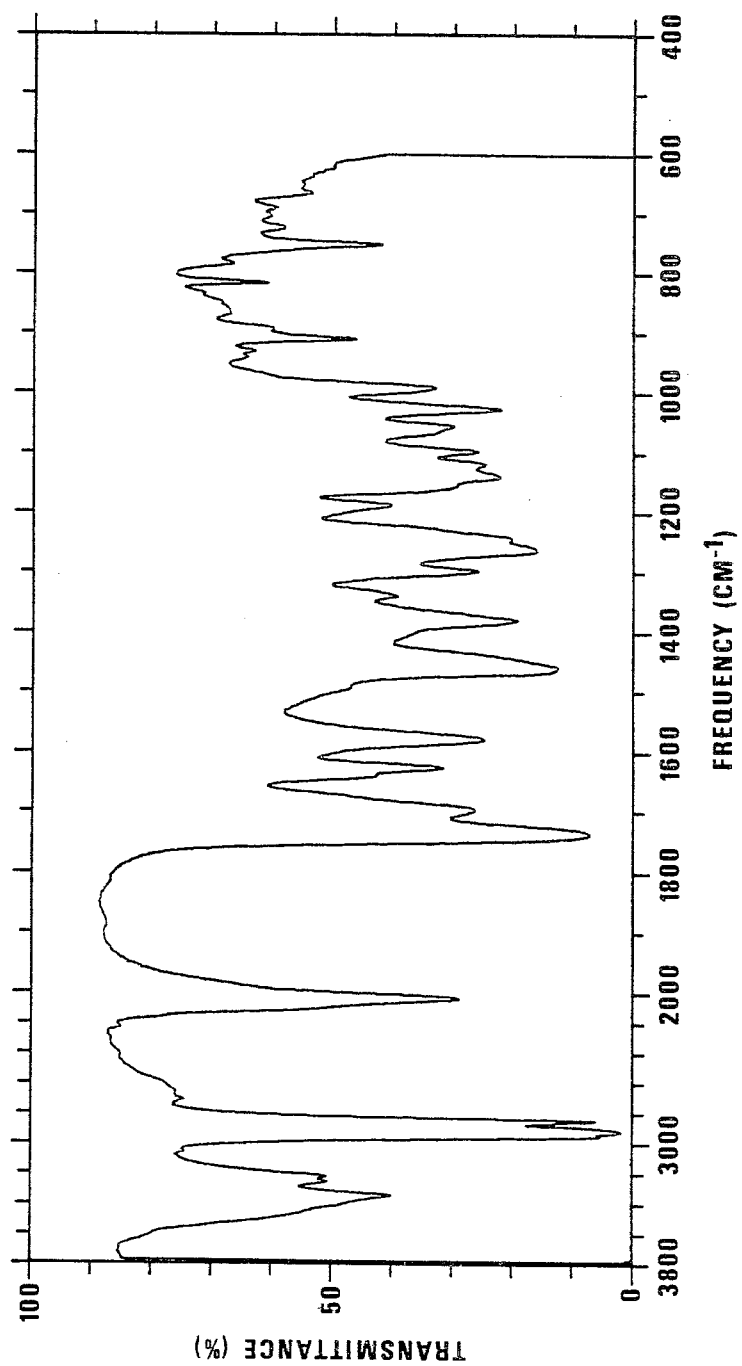

Paulomycin A has a characteristic infrared absorption spectrum in a mineral oil mull as shown in FIG. 1 of the drawings. Peaks are observed at the following wave lengths:

| Band Frequency[1] | Intensity[2] | Band Frequency | Intensity |
|---|---|---|---|
| 3356 | 40 | 1241 | 20 |
| 3266 | 51 | 1187 | 40 |
| 3230 | 51 | 1153 | 29 |
| 3072 | 74 | 1138 | 22 |
| 2954 | 4 | 1118 | 24 |
| 2923 | 2 | 1097 | 25 |
| 2870 | 12 | 1055 | 29 |
| 2854 | 5 | 1026 | 21 |
| 2724 | 75 | 990 | 32 |
| 2672 | 76 | 940 | 65 |
| 2248 | 85 | 931 | 63 |
| 2050 | 29 | 910 | 46 |
| 1735 | 7 | 894 | 60 |
| 1695 | 26 | 868 | 67 |
| 1640 | 42, sh. | 834 | 71 |
| 1626 | 31 | 818 | 61 |
| 1579 | 24 | 785 | 66 |
| 1491 | 47, sh. | 751 | 41 |
| 1457 | 12 | 723 | 58 |
| 1378 | 19 | 703 | 60 |
| 1340 | 39 | 665 | 53 |
| 1296 | 25 | | |
| 1261 | 15 | | |

[1]Wavenumbers (cm$^{-1}$)
[2]Percent transmittance (% T), sh. = shoulder
Intensity at 3800 cm$^{-1}$ is 84.9% T.
Minimum intensity at 1855 cm$^{-1}$ is 88.7% T.

Paulomycin A also has a characteristic infrared absorption spectrum when pressed in a KBr pellet. Peaks are observed at the following wave lengths:

| Band Frequency[1] | Intensity[2] | Band Frequency | Intensity |
|---|---|---|---|
| 3467 | 34, sh. | 1153 | 17, sh. |
| 3421 | 29 | 1137 | 13 |
| 3270 | 37 | 1117 | 14 |
| 3236 | 39 | 1098 | 15 |
| 3072 | 63 | 1055 | 17 |
| 2946 | 35 | 1026 | 11 |
| 2880 | 49 | 991 | 21 |
| 2831 | 59 | 943 | 54 |
| 2736 | 65 | 931 | 54 |
| 2245 | 69 | 909 | 34 |
| 2047 | 19 | 897 | 45, sh. |
| 1735 | 2 | 869 | 53 |
| 1701 | 15 | 834 | 60 |
| 1640 | 28, sh. | 816 | 51 |
| 1625 | 22 | 785 | 57 |
| 1578 | 14 | 751 | 37 |
| 1490 | 37, sh. | 728 | 58 |
| 1454 | 16 | 702 | 57, sh. |
| 1384 | 15 | 690 | 55 |
| 1376 | 18, sh. | 666 | 52 |
| 1340 | 30 | 639 | 55 |
| 1296 | 16 | 624 | 55 |
| 1261 | 9 | 603 | 53 |
| 1244 | 12, sh. | 527 | 58 |
| 1188 | 27 | 487 | 47 |

Figure 2:
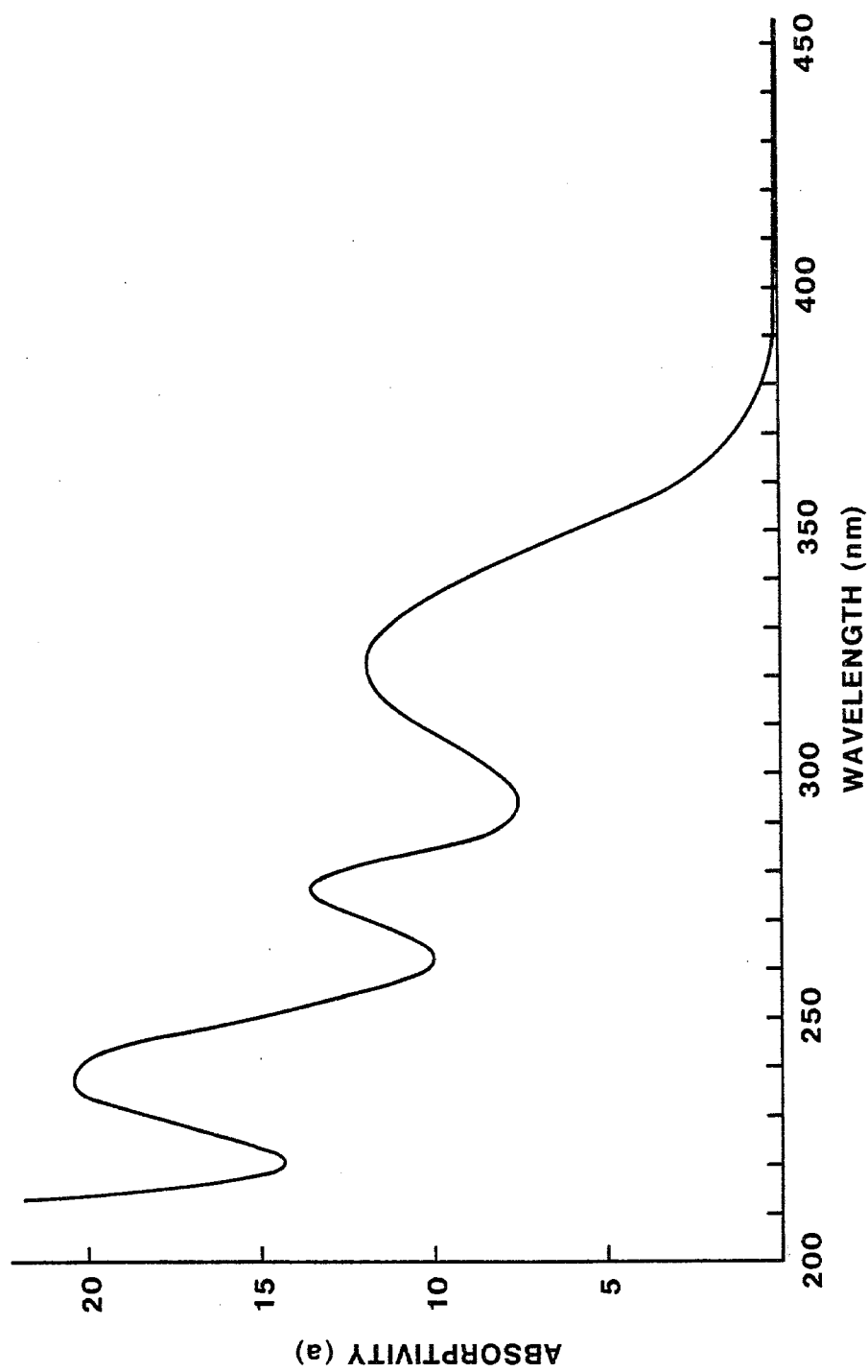

[1]Wavenumbers (cm$^{-1}$)
[2]Percent transmittance (% T), sh. = shoulder
Intensity at 3800 cm$^{-1}$ 69.9% T
Minimum intensity at 1905 cm$^{-1}$ is 72.8% T Ultraviolet Absorption Spectrum The UV spectrum of paulomycin A is shown in FIG. 2 of the drawings. The solution of antibiotic in 95% ethanol displayed absorption as follows:

| λ max | (a) |
|---|---|
| 236 nm | (20.57) |
| 276 | (13.76) |
| 322 | (12.33) |

Proton Magnetic Resonance ($^1$H-NMR)Spectrum

Figure 3:
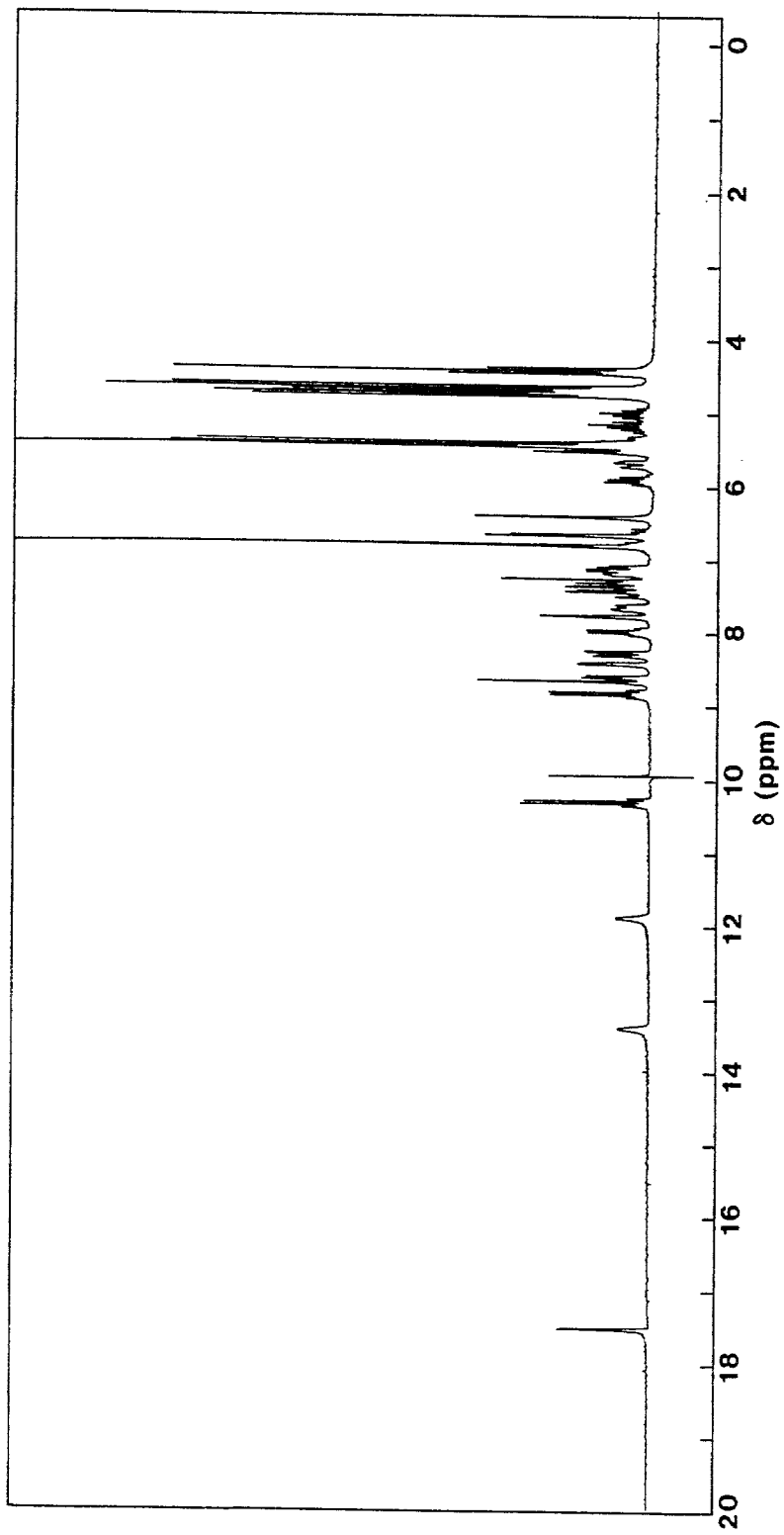

The $^1$-H-NMR spectrum of paulomycin A at 100 MHZ is shown in FIG. 3 of the drawings. The $^1$H-NMR spectrum was observed on a Varian XL-100-15 Spectrometer on a solution (ca. 0.5 ml., ca. 150 mg./ml.) of the sample of the antibiotic in deutero-dimethylsulfoxide (d$_6$-DMSO). The spectrum was calibrated against internal tetramethylsilane and frequencies were recorded in ppm downfield from tetramethylsilane.

Melting Point: 95°–105° C.

Optical Rotation: $[\alpha]_D^{25}$, +27° (c, 0.9435, CHCl$_3$) $[\alpha]_D^{25}$, −22° (c, 0.9555, methanol).

Titration Data: pKa, 7.4; Eq.wt. 808 Solvent, 60% aq. EtoH; titrant, KOH

Elemental Analysis: C, 48.77; H, 5.73; N, 3.29; S, 4.39; O (by difference), 37.82. Calcd. for $C_{34}H_{46}N_2SO_{17}$: C, 51.90; H, 5.85; N, 3.56; S, 4.07; O (by difference), 34.60.

Solubilities: Highly soluble in methanol, ethanol and other alcohols, acetone and other ketones, ethyl acetate and other esters, chloroform, methylene chloride, acetonitrile, DMF, DMSO, and the like. Relatively insoluble in saturated hydrocarbon solvents and water.

Electrophorectic Anaylsis: pH 1.8, +0.14; pH 8.7, −2.30.

Biological Properties of Paulomycin A

Antitumor (in vitro) Activity: L-1210; $ID_{50}$, 3.4 mcg./ml.; $ID_{90}$, 9.0 mcg./ml.

Antimicrobial Spectrum of Paulomycin A

Paulomycin A is active against various Gram-positive bacteria as shown in the following table:

Assay

The antibacterial assay is a standard microplate agar assay using PYG agar, pH 6. PYG agar consists of the following ingredients:

| | |
|---|---|
| Peptone | 10 g./l. |
| Yeast extract | 5 g./l. |
| Glucose | 1 g./l. |
| Agar | 15 g./l. |
| Distilled water, q.s. | 1 l. |

The MIC is determined by standard methods. The inocula are overnight cultures of the test organisms, diluted so that the final population contains approximately $10^5$ cells/ml. The agar plates are incubated at 28° to 37° C. for 24 hours. The lowest antibiotic concentration which allows no growth=MIC or minimum inhibitory concentration.

| Organism | | Minimum Inhibitory Concentration (mcg/ml) |
|---|---|---|
| S. aureus | UC 76 | 0.125 |
| | 6685 | 0.25 |
| | 6690 | 0.25 |
| S. pyogenes | 152 | |
| S. pneumoniae | 41 | |
| S. faecalis | 694 | 15.6 |
| Enterococcus sp. | 701 | 1.0 |
| E. coli | 45 | 125 |
| K. pneumoniae | 58 | 125 |
| Ps. aeruginosa | 95 | 125 |
| S. schottmuelleri | 126 | 125 |
| S. marcescens | 131 | 62.5 |
| S. flexneri | 143 | 62.5 |
| P. stuartii | 6570 | 62.5 |
| E. cloacae | 6783 | 250 |

"UC" is a registered trademark of the Upjohn Company Culture Collection. These cultures can be obtained from the Upjohn Company in Kalamazoo, Michigan, upon request.

Chemical and Physical Properties of Paulomycin B

Infrared Absorption Spectrum

Figure 4:
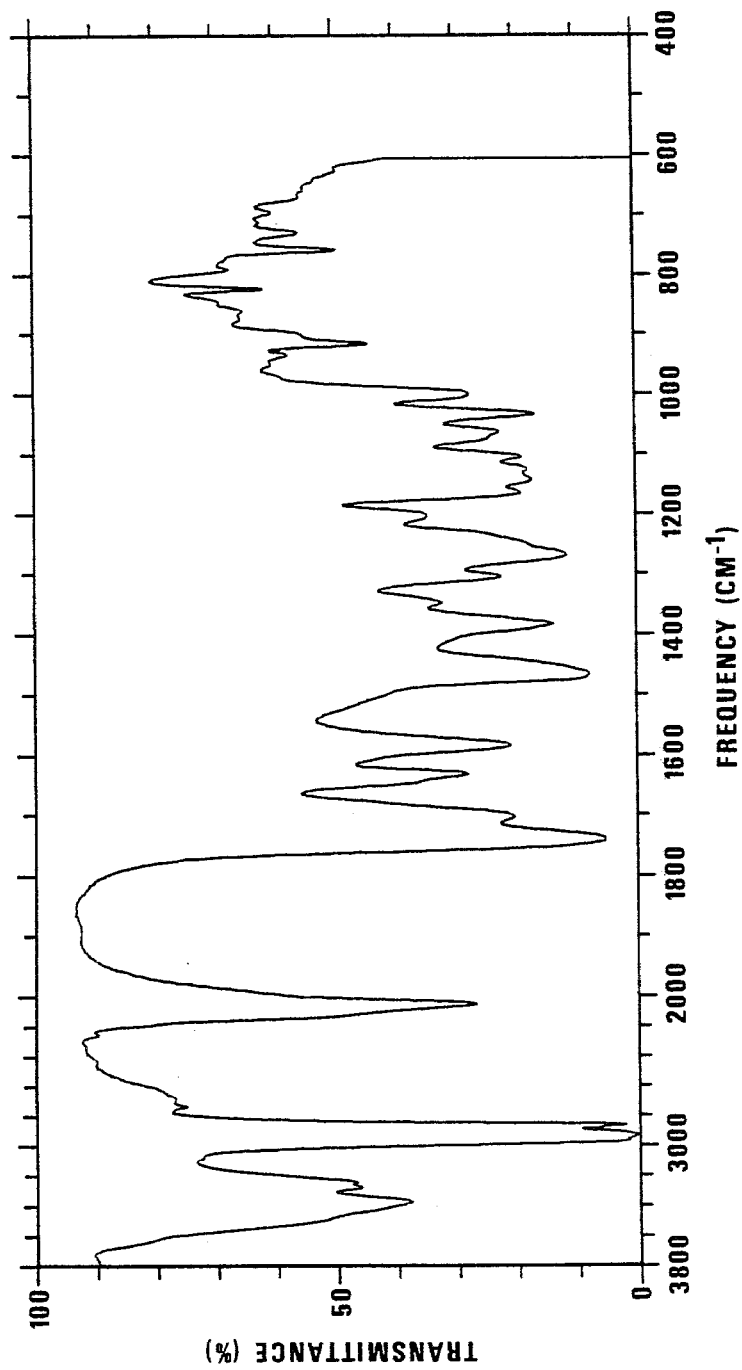

Paulomycin B has a characteristic infrared absorption spectrum in a mineral oil mull as shown in FIG. 4 of the drawings. Peaks are observed at the following wave lengths:

| Band Frequency[1] | Intensity[2] | Band Frequency | Intensity |
|---|---|---|---|
| 3365 | 38 | 1157 | 18 |
| 3267 | 46 | 1135 | 17 |
| 3233 | 47 | 1118 | 18 |
| 2953 | 2 | 1098 | 18 |
| 2923 | 0 | 1065 | 23, sh. |
| 2868 | 6, sh. | 1056 | 22 |
| 2854 | 2 | 1026 | 16 |
| 2727 | 75 | 996 | 27, sh. |
| 2674 | 77 | 992 | 27 |
| 2248 | 90 | 944 | 60 |
| 2047 | 27 | 929 | 57 |
| 1735 | 5 | 910 | 44 |
| 1696 | 20 | 897 | 55, sh. |
| 1627 | 27 | 869 | 65 |
| 1518 | 20 | 855 | 64 |
| 1457 | 7 | 839 | 69 |
| 1377 | 13 | 817 | 61 |
| 1342 | 32 | 784 | 67 |
| 1297 | 22 | 751 | 49 |
| 1261 | 11 | 721 | 55 |
| 1243 | 18, sh. | 690 | 60 |
| 1197 | 34 | 664 | 55 |

[1]Wavenumbers (cm$^{-1}$)
[2]Percent transmittance (% T), sh. = shoulder
Intensity at 3800 cm$^{-1}$ is 89.8% T
Minimum intensity at 1846 cm$^{-1}$ is 93.6% T.

Paulomycin B also has a characteristic infrared absorption spectrum when pressed in a KBr pellet. Peaks are observed at the following wave lengths:

| Band Frequency[1] | Intensity[2] | Band Frequency | Intensity |
|---|---|---|---|
| 3473 | 34, sh. | 1157 | 14 |
| 3419 | 28 | 1136 | 13 |
| 3390 | 29, sh. | 1118 | 13 |
| 3273 | 37 | 1099 | 14 |
| 3240 | 39, sh. | 1055 | 16 |
| 3075 | 69 | 1026 | 11 |
| 2941 | 38 | 995 | 22, sh. |
| 2831 | 59 | 991 | 21 |
| 2729 | 65 | 943 | 53 |
| 2238 | 70, sh. | 928 | 50 |
| 2046 | 20 | 909 | 36 |
| 1735 | 2 | 897 | 46, sh. |
| 1700 | 14 | 869 | 53 |
| 1638 | 28, sh. | 855 | 53 |
| 1626 | 22 | 840 | 58, sh. |
| 1578 | 15 | 816 | 52 |
| 1490 | 35, sh. | 784 | 58 |
| 1450 | 17 | 751 | 43 |
| 1385 | 16 | 729 | 59 |
| 1372 | 18 | 702 | 58, sh. |
| 1341 | 28 | 691 | 55 |
| 1296 | 18 | 666 | 54 |
| 1261 | 8 | 624 | 55 |
| 1243 | 13, sh. | 602 | 53 |
| 1195 | 28 | 490 | 46 |

[1]Wavenumbers (cm$^{-1}$)
[2]Percent transmittance (% T), sh. = shoulder
Intensity at 3800 cm$^{-1}$ is 70.2% T
Minimum intensity at 1911 cm$^{-1}$ is 74.0% T.

Ultraviolet Absorption Spectrum

Figure 5:
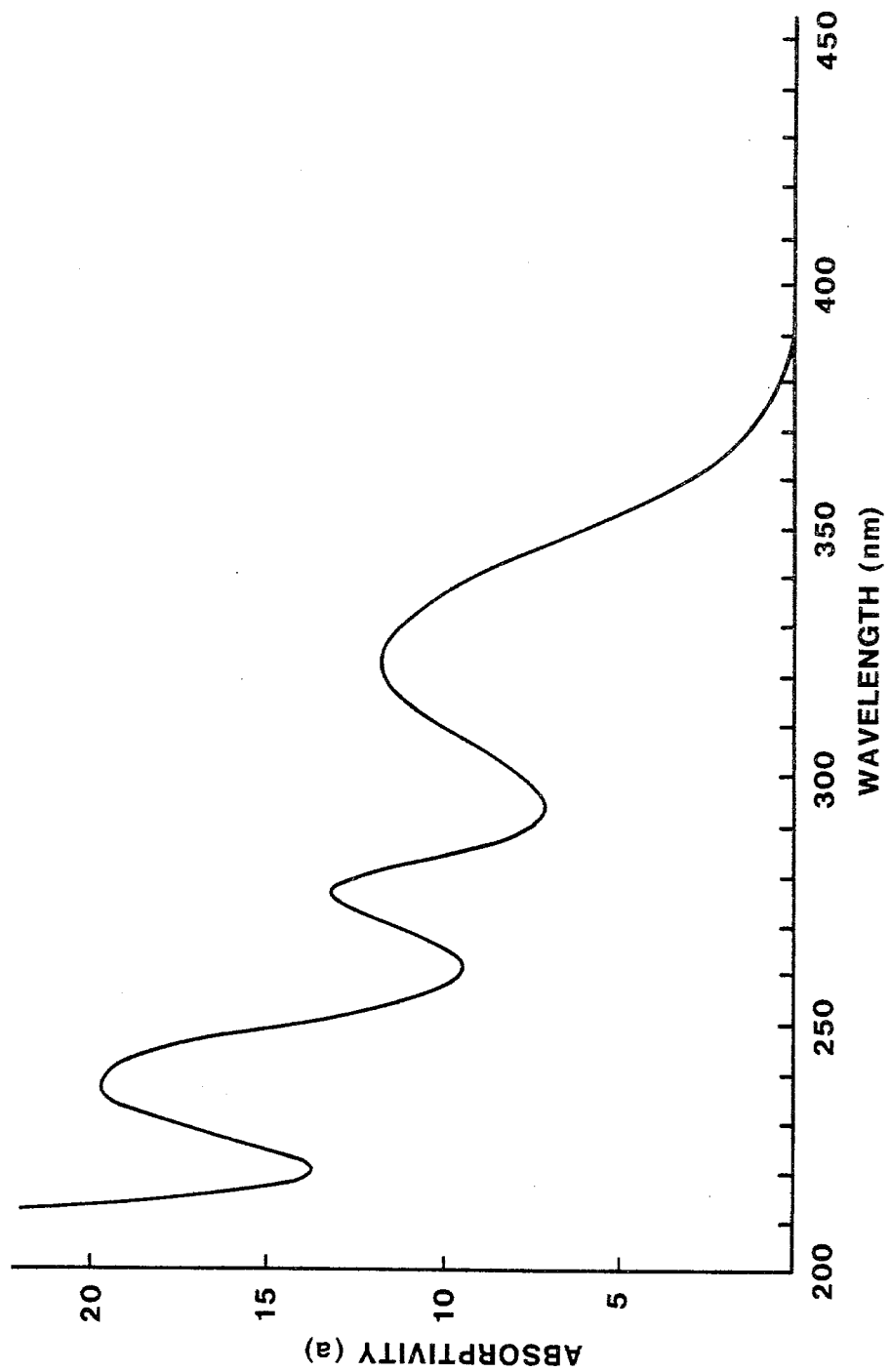

The UV spectrum of paulomycin B is shown in FIG. 5 of the drawings. The solution of antibiotic in 95% ethanol displayed absorption as follows:

| λ max | (a) |
|---|---|
| 236 nm | (20.29) |
| 276 | (13.51) |
| 322 | (11.97) |

Proton Magnetic Resonance ($^1$H-NMR) Spectrum

Figure 6:
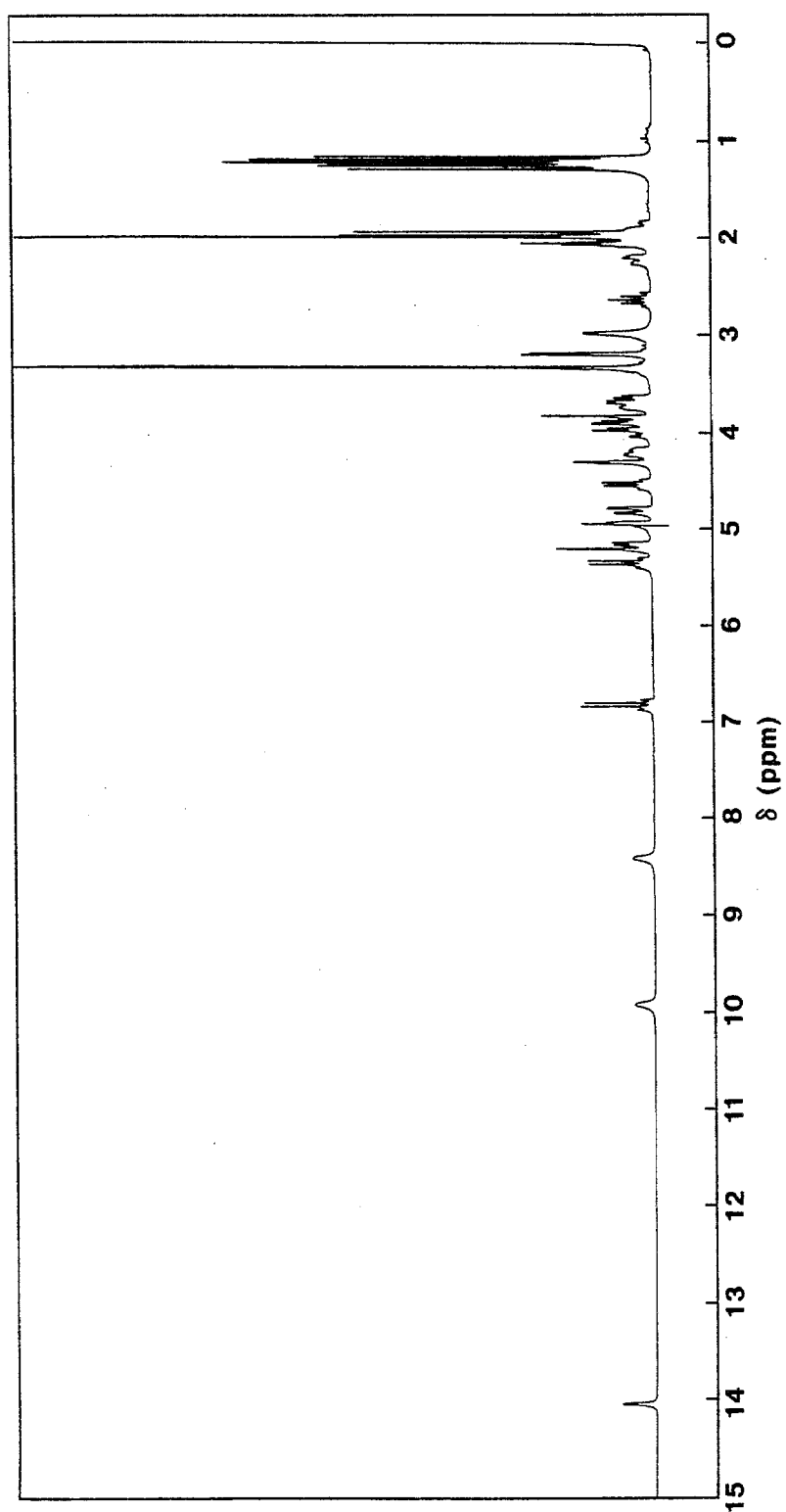

The $^1$-H-NMR spectrum of paulomycin B at 100 MHZ is shown in FIG. 6 of the drawings. The $^1$H-NMR spectrum was observed on a Varian XL-100-15 Spectrometer on a solution (ca. 0.5 ml., ca. 150 mg./ml.) of the sample of the antibiotic in deutero-dimethylsulfoxide ($d_6$-DMSO). The spectrum was calibrated against internal tetramethylsilane and frequencies were recorded in ppm downfield from tetramethylsilane.

Melting Point: 105.6°–143° C. with decomposition.

Optical Rotation: $[\alpha]_D^{25}$, +19° (c, 0.798, CHCl$_3$) $[\alpha]_d^{25}$, −28° (c, 0.850, methanol)

Titration Data: pKa, 7.4; Eq.wt., 791. Solvent: 60% ethanol; titrant, KOH.

Elemental Analysis: C, 50.82; H, 5.71; N, 3.51; S, 4.14; O (by difference) 35.82. Calcd for $C_{33}H_{44}N_2SO_{17}$; C, 51.29; H, 5.69; N, 3.62; S, 4.14; O (by difference) 35.23.

Solubilities: Highly soluble in methanol, ethanol and other alcohols, acetone and other ketones, ethyl acetate and other esters, chloroform, methylene chloride, acetonitrile, DMF, DMSO, and the like. Relatively insoluble in saturated hydrocarbon solvents and water.

Electrophorectic Analysis: pH 1.8+0.15; pH B.7 −0.92.

Biological Properties of Paulomycin B

Antitumor (in vitro) Activity: L-1210; ID$_{50}$, 8.6 mcg./ml.; ID$_{90}$, 21 mcg./ml.

Antimicrobial Spectrum of Paulomycin B

Paulomycin B is active against various Gram-positive bacteria as shown in the following table.

Assay. The antibacterial assay is a standard microplate agar assay using PYG agar, pH 6. The MIC is determined by standard methods. The inocula are overnight cultures of the test organisms, diluted so that the final population contains approximately $10^5$ cells/ml. The agar plates are incubated at 28° to 37° C. for 24 hours. The lowest antibiotic concentration which allows no growth=MIC or minimum inhibitory concentration.

| Organism | | Minimum Inhibitory Concentration (mcg/ml) |
|---|---|---|
| S. aureus | UC 76 | 0.50 |
|  | 6685 | 0.50 |
|  | 6690 | 2.0 |
| S. pyogenes | 152 |  |
| S. pneumoniae | 41 |  |
| S. faecalis | 694 | 125 |
| Enterococus sp. | 701 | 31.2 |
| E. coli | 45 | 250 |
| K. pneumoniae | 58 | 250 |
| Ps. aeruginosa | 95 | 250 |
| S. schottmuelleri | 126 | 500 |
| S. marcescens | 131 | 250 |
| S. flexneri | 143 | 250 |
| P. stuartii | 6570 | 250 |
| E. cloacae | 6783 | 500 |

Figure 7:
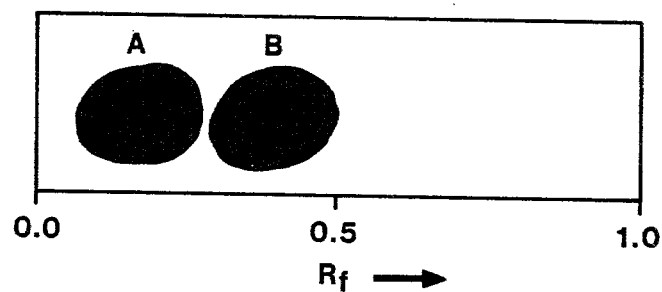

Comparison of paulomycin A and B on thin layer chromatography is as shown in FIG. 7 of the drawings.

Reference to the Drawings

FIG. 1: Infrared Absorption Spectrum of Paulomycin A in a Mineral Oil Mull.

FIG. 2: Ultraviolet Absorption Spectrum of Paulomycin A.

FIG. 3: Proton Magnetic Resonance Spectrum of Paulomycin A.

FIG. 4: Infrared Absorption Spectrum of Paulomycin B in a Mineral Oil Mull.

FIG. 5: Ultraviolet Absorption Spectrum of Paulomycin B.

FIG. 6: Proton Magnetic Resonance Spectrum of Paulomycin B.

FIG. 7: Thin layer Chromatographic Comparison of Paulomycin A and B.

THE MICROORGANISM

The man-made, biologically pure culture of the newly-discovered strain of S. paulus useful in the subject invention proces is S. paulus, strain 273, NRRL 12251.

A subculture of this microorganism can be obtained from the permanent collection of the Northern Regional Research Laboratory, U.S. Department of Agriculture, Peoria, Ill., U.S.A. Its accession number in this depository is NRRL12251. It should be understood that the availability of the culture does not constitute a license to practice the subject invention in derogation of patent rights granted with the subject instrument by governmental action.

The microorganism of this invention was studied and characterized by Alma Dietz and Grace P. Li of The Upjohn Research Laboratories.

S. paulus strain 273, NRRL 12251, can only be differentiated from S. paulus, NRRL 8115 by the ability of S. paulus strain 273 to produce higher fermentation titers of antibiotic U-43,120. As disclosed above, this antibiotic has been found to be a mixture of paulomycin A and B. It is because of this fermentation production difference that the microbe of this invention is considered to be a strain of S. paulus, NRRL 8115.

The taxonomy of S. paulus, NRRL 8115 is disclosed in U.S. Pat. No. 3,988,441. The same taxonomy can be used to describe S. paulus strain 273, NRRL 12251.

The compound of the invention process is produced when the elaborating organism is grown in an aqueous nutrient medium under submerged aerobic conditions. It is to be understood, also, that for the preparation of limited amounts, surface cultures and bottles can be employed. The organism is grown in a nutrient medium containing a carbon source, for example, an assimilable carbohydrate, and a nitrogen source, for example, an assimilable nitrogen compound or proteinaceous material. Preferred carbon sources include glucose, brown sugar, sucrose, glycerol, starch, cornstarch, lactose, dextrin, molasses, and the like. Preferred nitrogen sources include cornsteep liquor, yeast, autolyzed brewer's yeast with milk solids, soybean meal, cottonseed meal, cornmeal, milk solids, pancreatic digest of casein, fish meal, distillers' solids, animal peptone liquors, meat and bone scraps, and the like. Combinations of these carbon and nitrogen sources can be used advantageously. Trace metals, for example, zinc, magnesium, manganese, cobalt, iron, and the like, need not be added to the fermentation media since tap water and unpurified ingredients are used as components of the medium prior to sterilization of the medium.

Production of the compound by the invention process can be effected at any temperature conducive to satisfactory growth of the microorganism, for example, between about 18° and 40° C., and preferably between about 20° and 28° C. Ordinarily, optimum production of the compound is obtained in about 3 to 15 days. The medium normally remains acid during the fermentation. The final pH is dependent, in part, on the buffers present, if any, and in part on the initial pH of the culture medium.

When growth is carried out in large vessels and tanks, it is preferable to use the vegetative form, rather than the spore form, of the microorganism for inoculation to avoid a pronounced lag in the production of the compound and the attendant inefficient utilization of the equipment. Accordingly, it is desirable to produce a vegetative inoculum in a nutrient broth culture by inoculating this broth culture with an aliquot from a soil, liquid $N_2$ agar plug, or a slant culture. When a young, active vegetative inoculum has thus been secured, it is transferred aseptically to large vessels or tanks. The medium in which the vegetative inoculum is produced can be the same as, or different from, that utilized for the production of the compound, so long as a good growth of the microorganism is obtained.

A variety of procedures can be employed in the isolation and purification of the compound of the subject invention from fermentation beers, for example, solvent extraction, partition chromatography, silica gel chromatography, liquid-liquid distribution in a Craig apparatus, adsorption on resins, and crystallization from solvents.

In a preferred recovery process the compound of the subject invention is recovered from its culture medium by separation of the mycelia and undissolved solids by conventional means, such as by filtration or centrifugation. The antibiotic is then recovered from the filtered or centrifuged broth by extraction. For the extraction of paulomycin from the filtered broth, water-immiscible organic solvents in which it is soluble, for example, chloroform, ethylene dichloride, ethyl acetate, and methylene chloride (preferred) can be used. Advantageously, the extraction is carried on after the filtered beer is adjusted to a pH of about 2 to 7 with a mineral acid. The methylene chloride extracts are combined and evaporated to dryness under vacuum.

The first step in purification of the methylene chloride extract, as described above, is the use of silica gel chromatography using as solvents ethyl acetate, ethyl acetate-ethanol-water, ethyl acetate-water, and chloroform-ethyl acetate. The active fractions from the silica gel column can be further purified by countercurrent distribution using cyclohexane-ethyl acetate, 95% ethanol-water (1:1:1:1) as the solvent system. Fractions from the countercurrent distribution can be subjected to further silica gel chromatography to obtain a more active preparation which is thus more pure. A final purification step to yield a pure crystalline product is conducted by using chloroform to crystallize the product from the silica gel chromatography.

Preparations of paulomycin can be purified by repeated silica gel chromatography, as described above, without resort to countercurrent distribution.

Paulomycin A can be isolated as an essentially pure crystalline preparation from paulomycin by use of partition chromatography using a solvent system consisting of dioxane-cyclohexane, pH 7.0–0.1 M phosphate buffer (35:65:8).

Paulomycin B can be isolated as an essentially pure crystalline preparation from paulomycin by countercurrent distribution using a solvent system consisting of acetone-ethyl acetate-hexane, pH 7.0–0.1 M phosphate buffer (6:1:6:2 v/v).

Salts of paulomycin A and B can be formed with inorganic cations, for example, sodium, potassium, lithium, and calcium, since both antibiotics are weakly acidic. Such salts can be prepared, as for example, by suspending the antibiotic in water, adding a dilute base until the pH of the solution is about 10.0 to 11.0, and freeze-drying the solution to provide a dried residue consisting of the paulomycin A or B salt. Salts of paulomycin A or B can be used for the same biological purposes as the parent compounds.

Hereinafter are described non-limiting examples of the process and products of the subject invention. All percentages are by weight, and all solvent mixture proportions are by volume unless otherwise noted.

EXAMPLE 1

A. Fermentation

A biologically pure culture of *Streptomyces paulus* strain 273, NRRL 12251, is used to inoculate a series of 500-ml. Erlenmeyer seed flasks, each containing 100 ml. of sterile seed medium consisting of the following ingredients:

| | |
|---|---|
| Glucose monohydrate | 25 g/l |
| Pharmamedia* | 25 g/l |
| Tap water q.s. | 1 liter |

*Pharmamedia is an industrial grade of cottonseed flour produced by Traders Oil Mill Company, Fort Worth, Texas.

The seed medium presterilization pH is 7.2. The seed inoculum is grown for 2 days at 28° C. on a Gump rotary shaker operating at 250 r.p.m. and having a 2½ inch stroke.

Seed inoculum (5%), prepared as described above, is used to inoculate a series of 500 ml. fermentation flasks containing 100 ml. of sterile fermentation medium consisting of the following ingredients:

| | |
|---|---|
| Glucose monohydrate | 22 g/l |
| Pharmamedia | 19 g/l |
| Dextrin | 20 g/l |
| Brewers yeast | 0–1 g/l |
| Ucon (defoamer) | 10 g/l |
| Tap water q.s. | 1 liter |

Note: pH was adjusted to 7.2 before sterilization.

The inoculated fermentation flasks are incubated at a temperature of 25° C. for 3 to 5 days while being shaken on a Gump rotary shaker operating at 250 r.p.m. and having a 2½ inch stroke. Foaming in the fermentation flasks is controlled by the antifoam agent UCON (a synthetic defoamer supplied by Union Carbide, N.Y., N.Y.)

A comparison of the paulomycin fermentation titers of *S. paulus*, NRRL 8115 and *S. paulus* strain 273, NRRL 12251 under identical fermentation conditions is as follows:

| | Anti-*S. lutea* (pH 6.0 phosphate buffer, 32° C.) Biounits per ml. | | | | |
|---|---|---|---|---|---|
| Culture | Day 1 | Day 2 | Day 3 | Day 4 | Day 5 |
| NRRL | 42 | 51 | 64 | 51 | 32 |
| NRRL 8115 | <1 | 3 | <1 | <1 | 8 |

The above results clearly show the superiority of *S. paulus* strain 273, NRRL 12251, in the fermentation production of paulomycin.

Antibiotic Assay

Fermentation beers are sedimented by centrifugation at ca. 3000×g. The supernatant fluids (clear beers) are assayed for antibiotic activity v.s. *S. lutea,* UC®130 using bioautographic or disc-plate methods. For bioautography, thin layer chromatography (tlc) is performed on Brinkman silica gel (Sil NHr plates) or on Brinkman cellulose (Cel 400) developed respectively in $CHCl_3$, $C_2H_5OH$ and $H_2O$ (25:30:5) or in 0.1 M potassium phosphate, pH 7. Clear beer anti-*S. lutea* biounit titers are obtained by a standard disc-plate assay.

A biounit (BU) is defined as the concentration of the antibiotic which gives a 20 mm zone of inhibition under the above assay conditions. Thus, if for example a fermentation beer, or other solution containing the antibiotic, needs to be diluted 1/100 to give a 20 mm zone of inhibition, the potency of such beer or solution is 100 BU per ml.

B. Recovery (1) Extraction

Whole beer, ca 4000 liters, obtained from a fermentation as described above, is adjusted to pH 2.8 with sulfuric acid and cooled to 16° C. in the fermentor. Celatom FW-40 filter aid (The Eagle Pitcher Co., Cincinnati, Ohio), 237 kg. is added and the mixture is filtered using a rotary vacuum filter. The filtered beer which contains 9% of the total bioactivity is discarded. The filter cake is slurried with 2000 liters ethyl acetate overnight then filtered through 40 chambers of a 30" press filter. The filtrate (ethyl acetate extract containing paulomycin) is concentrated to 64 liters. This concentrate is mixed with 17.5 kg. of Harborlite 2000 M (Harborlite Corporation, Escondido, Cal.) and the wet mixture was dried in a vacuum overnight at 40° C. The dried Harborlite-paulomycin mixture is used as described below:

(2) Purification - Harborlite Leaching Column Chromatography

The dried harborlite-paulomycin mixture, obtained as described above, is loaded into a 14" column partially filled with dried heptane and packed under atmospheric pressure. The column is eluted at a rate of 1.5 liter per minute and fractions (as shown below) are collected.

| Fraction Number | Eluting Solvent | Volume (l) | Percent of Bioactivity of Starting Material |
|---|---|---|---|
| 1 | Heptane | 107 | 4 |
| 2 | Heptane-Ethyl acetate (97:3) | 103 | 1 |
| 3 | Heptane-Ethyl acetate (94:6) | 93 | 1 |
| 4 | Heptane-Ethyl acetate (91:9) | 93 | 3 |
| 5 | Heptane-Ethyl acetate (88:12) | 93 | 7 |
| 6 | Heptane-Ethyl acetate (80:15) | 93 | 15 |
| 7 | Heptane-Ethyl acetate (80:15) | 93 | 17 |
| 8 | Heptane-Ethyl acetate (80:15) | 93 | 13 |
| 9 | Heptane-Ethyl acetate (80:15) | 93 | 17 |
| 10 | Heptane-Ethyl acetate (80:15) | 93 | 15 |
| 11 | Heptane-Ethyl acetate (80:15) | 93 | 11 |
| 12 | Heptane-Ethyl acetate (80:15) | 93 | 10 |
| 13 | Heptane-Ethyl acetate (80:15) | 93 | 3 |
| 14 | Heptane-Ethyl acetate (80:15) | 93 | 1 |
| 15 | Heptane-Ethyl acetate (80:15) | 93 | <1 |

Fractions are pooled as follows:
Pool A, Fractions 10 and 11.
Part B, Fractions 7, 8, and 12.
Part C, Fractions 6, 9, 13 and 14.
Part D, Fractions 5 and 15.

The pools are concentrated to dryness in vacuo. Crystalline paulomycin is obtained from pools A, B and C by the following procedures.

(3) Crystallization of paulomycin

The residue obtained from pool A contains ca 44 g. of paulomycin. This material is dissolved in 4.2 l. of methylene chloride. Heptane, 4.2 l., is added under stirring. An oily material precipitates and is removed by decantation. The oil is dissolved in acetone and added to the supernatant. Then, an additional 8.4 liter of heptane is added and the mixture is stored at 5° C. overnight. Crystalline material precipitated is isolated by filtration and dried [Prep. A, 47.7 g., containing ca 29.7 g. of paulomycin]. The filtrate which contains ca 7.9 g. of paulomycin is concentrated to a small volume (ca 3 liter) and is stored for further processing and isolating the remaining paulomycin.

The residue from pool B is treated as described above to give Preparation B, 56.1 g. of crystals containing ca 43.1 g. of paulomycin. The mother liquors contain ca 3.8 g. of paulomycin.

The residue from pool C is treated as described for pool A to give Preparation C, 70.5 g. of crystals containing ca 35.1 g. of paulomycin. The mother liquors contain 7.6 g. of paulomycin.

(4) Combination of Crystalline Preparations Recrystallization

Preparations, A, B and C are combined to give prep. 64.1, 174.3 g.

Preparation 64.1 is dissolved in chloroform (37.5 ml./g. of preparation 64.1) by heating on a steam bath. The solution is clarified by filtration and the clear solution is mixed with ether (18.75 ml. per g. of −64.1) and heptane (18.75 ml. per g. of −64.1) under heating on a steam bath. The slightly cloudy solution is allowed to stand at room temperature for 2 hours then at 5° C. for 20 hours. Crystalline paulomycin is isolated by filtration (prep. −64.2, 110.61 g.). The mother liquors give prep. −64.3, 60 g. by concentration to dryness in vacuo.

Crystalline paulomycin (prep −64.2), isolated as described above, is recrystallized from chloroform-ether-heptane as described above to give preparation −65.1, 86.13 g. The new mother liquors give preparation −65.2. Preparation −65.1 contains 66.8% paulomycin A and 32.9% paulomycin B as determined by HPLC.

EXAMPLE 2

Paulomycin A-Isolation by Partition Chromatography

Four hundred g. of dicalite-diatomite is slurried with upper phase of the system consisting of dioxane-cyclohexane-pH 7.0-0.1 M phosphate buffer (35:65:8). Lower phase, 160 ml., is added and the whole is mixed for 20 minutes. The slurry is added into a column and packed to a constant height under 3 Atm. pressure.

The starting material 1 g. of crude crystalline paulomycin, obtained as described above, is dissolved in 5 ml.

of lower phase and 15 ml. of upper phase, mixed with 15 g. of dicalite, and added on the top of the column. The column is eluted with the upper phase. Fractions of 10 ml. are collected at a rate of 4 ml./min. The chromatography is followed by testing for bioactivity vs. *S. lutea* and by tlc (Brinkman's Cellulose 400; pH 7.0 phosphate buffer). Fractions containing paulomycin A are combined and concentrated to dryness. The residue is crystallized from 5 ml. of chloroform and 5 ml. of ether to give 120 mg. of an essentially pure crystalline preparation of paulomycin A.

EXAMPLE 3

Paulomycin B-Isolation by Countercurrent Distribution

Solvent: acetone-ethyl acetate-hexane-pH 7.0–0.1 M phosphate buffer (6:1:6:2 v/v).

Crude crystalline paulomycin, 3.0 g., is dissolved in both phases of the solvent system and introduced in 4 tubes of an all-glass 500-tube countercurrent distribution apparatus. After 800 transfers, the distribution is analyzed by testing for bioactivity vs. *Sarcina lutea* and by tlc (Brinkman's Cellulose 400, pH 7.0 phosphate buffer). Fractions containing paulomycin B only (fraction 210–273) are combined and the solution is adjusted to pH 5.5 with 1 N aqueous hydrochloric acid. The lower phase is extracted 3 times with ⅓ ethyl acetate volume each time. The ethyl acetate extracts are combined with the upper phase and the combined solution is concentrated to dryness in vacuo. The residue is crystallized from 15 ml. chloroform, 7.5 ml. of ether and 7.5 ml. of heptane to give 290 mg. of an essentially pure crystalline preparation of paulomycin B. Recrystallization from the same solvents yielded 170 mg. of an essentially pure crystalline preparation of paulomycin B.

We claim:

1. Essentially pure crystalline paulomycin A, which is characterized as follows:
    (a) active against Gram-positive bacteria;
    (b) melting point: 95°–105° C.;
    (c) optical rotation $[\alpha]_D^{25}$, $-22°$ (c, 0.9555, methanol); $[\alpha]_D^{25}$, $+27°$ (C, 0.9435, CHCl$_3$);
    (d) elemental analysis: C, 48.77; H, 5.73; N, 3.29; S, 4.39; O (by difference), 37.82;
    (e) titration: pKa, 7.4; Eq.wt. 808, in 60% aqueous EtOH; titrant, KOH;
    (f) a characteristic infrared absorption spectrum as shown in FIG. 1 of the drawings;
    (g) a characteristic ultraviolet absorption spectrum as shown in FIG. 2 of the drawings; and,
    (h) a characteristic proton magnetic resonance spectrum as shown in FIG. 3 of the drawings, or inorganic cationic salts thereof.

2. Essentially pure crystalline paulomycin B which is characterized as follows:
    (a) active against Gram-positive bacteria;
    (b) melting point: 105.6°–143° C. with decomposition;
    (c) optical rotation $[\alpha]_D^{25}$, $+19°$ (c, 0.798, CHCL$_3$); $[\alpha]_D^{25}$, $-28°$ (c, 0.850, methanol);
    (d) elemental analysis: C, 50.82; H, 5.71; N, 3.51; S, 4.14; O (by difference), 35.82;
    (e) titration: pKa, 7.4; Eq.wt. 791, in 60% EtOH; titrant, KOH;
    (f) a characteristic infrared absorption spectrum as shown in FIG. 4 of the drawings;
    (g) a characteristic ultraviolet absorption spectrum as shown in FIG. 5 of the drawings; and,
    (h) a characteristic proton magnetic resonance spectrum as shown in FIG. 6 of the drawings, or inorganic cationic salts thereof.

3. An improved fermentation process for preparing the antibiotic paulomycin, which comprises cultivating *Streptomyces paulus* strain 273, having the identifying characteristics of NRRL 12251, in an aqueous nutrient medium containing a source of assimilable nitrogen under aerobic conditions until substantial antibiotic activity is imparted to said medium.

4. A process for preparing essentially pure crystalline paulomycin A, the compound defined in claim 1, which comprises subjecting a preparation of paulomycin to partition chromatography using a solvent system consisting of dioxane-cyclohexane-pH 7.0–0.1 M phosphate buffer (35:65:8 v/v), and crystallizing paulomycin A as an essentially pure form from fractions containing paulomycin A.

5. A process, according to claim 4, wherein said paulomycin preparation is crude crystalline paulomycin.

6. A process, according to claim 4, wherein equal parts of chloroform and ether are used to crystallize paulomycin A from fractions containing paulomycin A.

7. A process for preparing essentially pure crystalline paulomycin B, the compound defined in claim 2, which comprises subjecting a preparation of paulomycin to countercurrent distribution using a solvent system consisting of acetone-ethyl acetate-hexane-pH 7.0–0.1 M phosphate buffer (6:1:6:2 v/v), and crystallizing paulomycin B as an essentially pure form from fractions containing paulomycin B.

8. A process, according to claim 7, wherein said paulomycin preparation is crude crystalline paulomycin.

9. A process, according to claim 7, wherein chloroform-ether-heptane (15:7.5:7.5 v/v) is used to crystallize paulomycin B from fractions containing paulomycin B.

10. A man-made biologically pure culture of the novel microorganism *Streptomyces paulus* strain 273, having the identifying characteristics of NRRL 12251, said culture being capable of producing the antibiotic paulomycin in a recoverable quantity upon fermentation in an aqueous nutrient medium containing assimilable sources of carbon, nitrogen and inorganic substances in a controlled environment.

* * * * *